United States Patent [19]

Kashdan

[11] Patent Number: 4,496,762
[45] Date of Patent: Jan. 29, 1985

[54] PROCESS FOR THE PREPARATION OF N-(2-(CYCLO-HEXEN-1-YL)ETHYL)-4-METHOXYBENZENEACETAMIDE

[75] Inventor: David S. Kashdan, Kingsport, Tenn.

[73] Assignee: Eastman Kodak Company, Rochester, N.Y.

[21] Appl. No.: 480,039

[22] Filed: Mar. 29, 1983

[51] Int. Cl.³ .................. C07C 103/76; C07C 102/08
[52] U.S. Cl. ..................................... 564/170; 546/74; 564/139
[58] Field of Search ....................... 564/170, 182, 139; 424/260; 546/74

[56] References Cited

U.S. PATENT DOCUMENTS 2,634,273  4/1953  Hellerbach ..................... 564/170 X
2,683,713  7/1954  Shepard ......................... 564/170 X
3,634,429  1/1972  Leimgruber et al. ............... 546/74
3,810,899  5/1974  Mohacsi et al. ................. 564/170 X

OTHER PUBLICATIONS

Stork et al., CA 55: 2596f, (1961).

Primary Examiner—Thomas A. Waltz
Attorney, Agent, or Firm—Clyde L. Tootle; Gary C. Bailey; Daniel B. Reece, III

[57] ABSTRACT

An improved method for preparing a compound having the formula

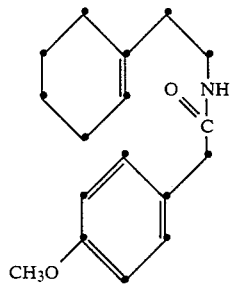

which is an intermediate in the preparation of dextromethorphan, the improved method comprises the steps of (A) hydrogenating a compound having the formula

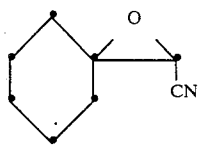

in the presence of a hydrogenation catalyst to obtain a compound having the formula

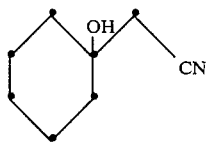

(B) hydrogenating the product of Step (A) in the presence of a hydrogen treated rhodium catalyst to obtain a compound having the formula

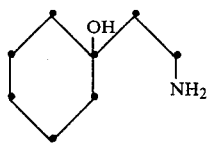

(C) reacting the product of Step (B) with 4-methoxyphenylacetic acid to obtain a mixture of compounds comprising

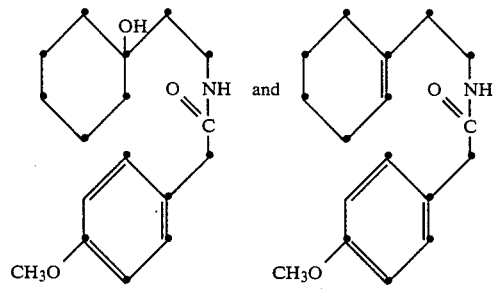

(D) dehydrating the product mixture of Step (C).

16 Claims, No Drawings

PROCESS FOR THE PREPARATION OF N-(2-(CYCLO-HEXEN-1-YL)ETHYL)-4-METHOXYBENZENEACETAMIDE

BACKGROUND OF THE INVENTION

This invention relates to an improved method for the preparation of N-[2-(cyclohexen-1-yl)ethyl]-4-methoxybenzeneacetamide, a useful intermediate in the preparation of dextromethorphan, an antitussive agent employed in cough syrups.

The preparation of dextromethorphan as with many pharmaceutically active compounds requires a plurality of chemical reaction steps and the formation of a number of intermediates. A key intermediate in the preparation of dextromethorphan is N-[2-(cyclohexen-1-yl)ethyl]-4-methoxybenzene acetamide having the structural formula

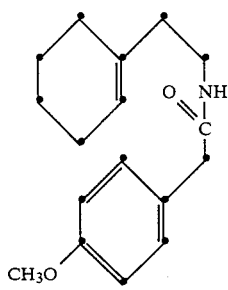

(V)

Heretofore there has been one principal commercial method for preparing this intermediate [see U.S. Pat. No. 3,634,429 and Helv. Chem. Acta, 34 1437 (1950)]. This method consists of converting cyclohexylidene cyanoacetic acid to 1-cyclohexenylacetonitrile which is reduced to the corresponding amine using lithium aluminum hydride. The amine derivative is then reacted with 4-methoxyphenyl acetic acid to obtain the desired intermediate (V). Because the use of lithium aluminum hydride is both expensive and hazardous an alternate, commercially attractive method is desirable. It has been found that the desired intermediate (V) can be obtained in good yield by a method which avoids the costly and potentially unsafe lithium aluminum hydride reduction step. The preparation of this intermediate is accomplished according to the following chemical reaction scheme:

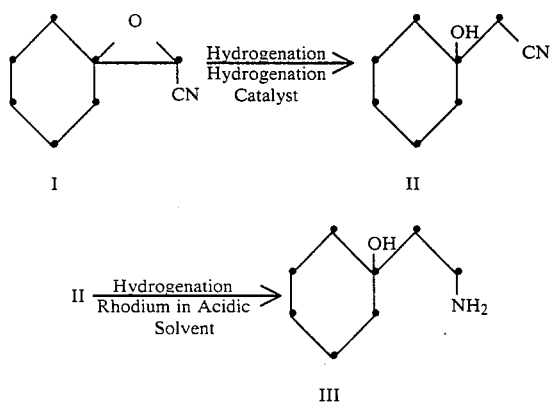

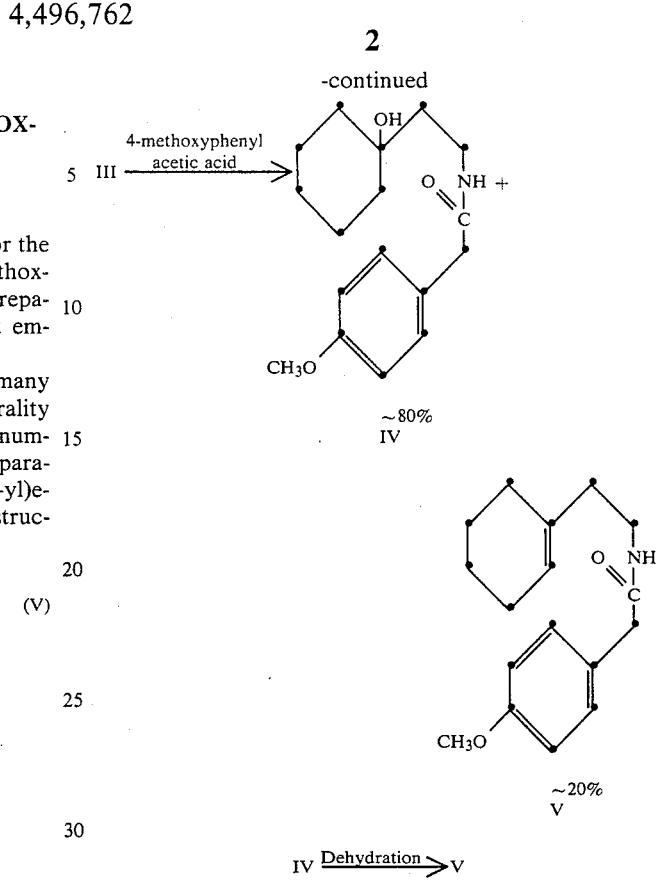

SUMMARY OF THE INVENTION

The process of the present invention concerns the preparation of N-[2-cyclohexen-1-yl)ethyl]-4-methoxybenzenacetamide. The process comprises the steps of (A) hyrogenating 2-cyano-1-oxaspiro[2]nonane in the presence of a hydrogenation catalyst to obtain 1-cyanomethylcyclohexanol, wherein the hydrogenation is discontinued after the uptake of about one mole equivalent of hydrogen; (B) hydrogenating the product of Step (A) in the presence of a hydrogen treated rhodium catalyst suspended in an acidic solvent to obtain 1-(2-aminoethyl)cyclohexanol; (C) reacting the product of Step (B) with 4-methoxyphenyl acetic acid to obtain a mixture of compounds comprising N-[2-(1-hydroxy-1-cyclohexyl)ethyl]-4-methoxybenzeneacetamide (IV) and N-[2-(cyclohexen-1-yl)-ethyl]-4-methoxybenzeneacetamide (V); (D) dehydrating the product mixture of Step (C).

DETAILED DESCRIPTION OF THE INVENTION

The starting material for this process, 2-cyano-1-oxaspiro[2]nonane, having formula (I), hereinafter referred to as an epoxynitrile, is a known compound and can readily be obtained by the condensation of chloroacetonitrile and cyclohexanone according to known chemical procedures.

Hydrogenation of the epoxynitrile to obtain cyanomethylcyclohexanol, having formula (II), hereinafter referred to as hydroxynitrile, is carried out in the presence of a hydrogenation catalyst. Examples of hydrogenation catalysts which may be used include platinum, palladium, Raney nickel and the like. The preferred catalyst for this hydrogenation step is platinum or palladium with palladium being most preferred. Generally, the catalyst may be unsupported or supported on any conventional carrier such as silica, alumina, carbon, calcium sulfate, barium sulfate and the like. The amount of catalyst employed typically will be about 0.01 to 2.0 weight percent based on the amount of epoxynitrile used, with about 0.5 weight percent being preferred.

This step of the process is most conveniently carried out in the presence of a solvent. Suitable solvents include the lower carbon alkanols ($C_1$–$C_4$) and lower carbon aliphatic carboxylic acids ($C_1$–$C_4$) Examples of the alkanol solvents are methanol, ethanol, 1-propanol, 2-propanol, and any of the butanols. Typical carboxylic acid solvents are acetic acid, propanoic acid and butyric acid.

The hydrogenation pressure of the reaction need not be elevated since the reaction is essentially complete in a matter of minutes. If desired, a moderately elevated pressure may be used. Generally a pressure up to about 50 psig will be sufficient. To achieve a maximum yield of hydroxynitrile and to avoid the formation of undersirable by-products such as imines, aminals and polymers thereof it is important that the period of hydrogenation be controlled, i.e., hydrogenation discontinued after the uptake of about one equivalent of hydrogen. On a small scale, such as in the experimental examples disclosed hereinafter, the period of uptake is about 10 minutes. Of course this time can be expected to vary depending on the volume of reactant, pressure, equipment and the like.

Step (B) of my process involves hydrogenating the hydroxynitrile product of Step (A) in the presence of a hydrogen treated rhodium catalyst in an acidic solvent. The rhodium catalyst can be unsupported or supported on any conventional support that is nonreactive with the solvent employed. Carriers such as silica, alumina, and carbon are among the more commonly used catalyst supports which can be used. The amount of catalyst employed will normally be about 0.1 to 2.5 weight percent based on the amount of hydroxynitrile with about 1.5 weight percent being preferred. The solvent used will normally be a lower carbon aliphatic carboxylic acid ($C_1$–$C_4$) or a combination alkanol/inorganic acid. The alkanols can be the same as those employed in Step (A) and the inorganic acids can be sulfuric acid, hydrochloric acid and the like.

This reaction step can generally be carried out without the use of elevated pressure although a moderately elevated hydrogenation pressure is preferred. Accordingly, a hydrogenation pressure up to about 500 psig can ordinarily be employed with a pressure of about 50 to 100 psig being preferred.

As indicated a hydrogen treated rhodium catalyst is employed in this process step, that is the rhodium metal is contacted with hydrogen, normally by introducing hydrogen into a suitable reactor vessel containing the rhodium metal and solvent. The contacting of the rhodium metal with hydrogen is ordinarily maintained for several minutes, i.e. 10 minutes is usually sufficient when conducted on a laboratory scale such as in the experimental examples disclosed hereinafter. It is particularly advantageous to the operation of this step to contact the rhodium metal with hydrogen before the hydroxynitrile is added to the solvent-catalyst mixture. While success of this step does not depend on contacting the catalyst with hydrogen prior to the addition of the hydroxynitrile, decreased yields of the desired hydroxyamine compound are obtained when the hydroxynitrile is added in whole or in part prior to contacting the catalyst with hydrogen. It is also particularly advantageous to control the rate of addition of the hydroxynitrile, that is to add the hydroxynitrile gradually or in increments to achieve maximum formation of the desired 1-(2-aminoethyl)cyclohexanol. In a typical set-up the solvent and catalyst are placed in a suitable reactor vessel. The reactor vessel is then pressurized with hydrogen, normally for several minutes, e.g., 10 minutes in the case of the experimental examples disclosed hereinafter. During this time it is advantageous to rock or shake the slurry of solvent and catalyst. The hydroxynitrile is then added to the reactor vessel in small individual portions or in a slow steady stream over a period of several hours. On a laboratory scale the addition time is normally about 3 to 15 hours. This time can naturally be expected to increase as the size of the operation increases. During the addition of the hydroxynitrile the hydrogenation pressure is maintained at about 50 to 100 psig. When conducted according to this typical set-up maximum yields of the desired hydroxyamine product normally can be obtained. However, if the hydroxynitrile is added too fast or all at once or if the catalyst is not first treated with hydrogen as previously described the yield and purity of the hydroxyamine are adversely affected and the formation of unwanted by-products increases.

Step (C) of my process is carried out according to known amidation procedures using conventional reaction conditions. The reaction of 1-(2-aminoethyl)cyclohexanol, having formula (III) and hereinafter referred to as hydroxyamine, and 4-methoxyphenyl acetic acid is carried out in an inert atmosphere, e.g., nitrogen, to avoid possible product decomposition. Water formed from the reaction is removed by azeotropic distillation. The mole ratio of hydroxyamine to 4-methoxyphenyl acetic acid will be about 1:1 to 1:1.2. The resulting product is a mixture of amides (IV) and (V) which are present in a ratio of about 4:1, respectively.

This process step is carried out in an inert solvent, preferably one capable of forming an azeotropic mixture with water. Typical solvents which can be employed are the inert aromatic hydrocarbons such as decalin, toluene, xylene, benzene and the like. The reaction temperature normally will be at reflux, the actual temperature depending on the boiling temperature of the solvent. Generally a temperature range of about 80° to 190° C. is suitable.

According to the process of Step D the mixture of compounds (IV) and (V) is dehydrated to obtain the desired product (V) in about 85% to 90% yield and containing about 5% or less of compound (IV). The conversion of the mixture of (IV) and (V) to predominantly (V) is accomplished by conventional dehydration methods. A typical method is by heating the mixture under reflux conditions while azeotropically removing water. Additionally the mixture may be dehydrated using known dehydrating agents such as sulfuric acid, phosphoric acid or dimethylsulfoxide. The preferred method for this step is by the use of a dehydrating agent, preferably dimethylsulfoxide. Typically the mixture of compounds (IV) and (V) is heated in the presence of dimethylsulfoxide in an inert atmosphere, e.g. nitrogen, at a temperature of about 95° to 115° C. Generally, about 1 to 10 moles of dimethylsulfoxide will be used per mole of (IV) and (V) combined. Isolation of the product (V) is achieved according to conventional techniques.

The following examples are given to further illustrate the invention, but it is to be understood that the invention is not to be limited in any way by the details described therein.

EXPERIMENTAL EXAMPLE 1

Demonstrating the Preparation of
2-Cyano-1-oxaspiro[2]-nonane (I)

A dry 500-ml three-necked round-bottom flask equipped with a mechanical stirrer, thermometer, dropping funnel, and nitrogen atmosphere was charged with 28.125 g. (0.373 mol) chloroacetonitrile, 31.5 g. (0.375 mol) cyclohexanone, and 50 ml tert-butyl alcohol. This solution was cooled in an ice bath while a filtered solution of 112 g. (0.40 mol) potassium t-butoxide in 170 ml t-butyl alcohol (distilled from $CaH_2$) was added dropwise over a five-hour period. The internal temperature was maintained between 8° and 15° C. During the addition, a precipitate (KCl) formed. The reaction mixture was allowed to stir for 16 hours.

The resulting slurry was concentrated in vacuo with moderate heating ($\sim 70°$ C.) and then dissolved in 50 ml water followed by ether extraction (3X 30 ml). The combined organic phases were dried ($Na_2SO_4$) and concentrated in vacuo to a red-brown oil weighing 39 g. Kugelrohr distillation (110° C., 0.5 mm) afforded a clear, colorless oil with some white solid present (pot residue: 0.90 g. red polymer). The distillate was taken up in hexane, filtered (0.79 g white solid), and evaporated to a clear colorless oil, homogeneous by TLC (3% MeOH in $CH_2Cl_2$) and GC (10% OV-101 on chrom WHP 80/100, $6' \times \frac{1}{8}''$ column), 36.9 g., 0.27 mol, 72% yield.

NMR ($CDCl_3$, TMS) δ 3.29 (S,1H), 1.9–1.3 (b,10H) MS E-29885BE m/e: 137,110 (−HCN).

EXPERIMENTAL EXAMPLE 2

Demonstrating the Preparation of
1-Cyanomethylcyclohexanol (II)

In a 250 ml Parr pressure vessel was placed 2.0 g. (0.0145 mol) of (I), 50 ml ethanol (8082), and 400 mg 5% Pd/C (Engelhardt) 1 weight % metal. The pressure vessel was placed on a Parr shaker and pressurized with 50 psi $H_2$. During the first five minutes, the $H_2$ uptake was extraordinarily rapid. The reaction was stopped after 10 minutes; TLC (3% MeOH/$CHCl_3$) showed that no starting material was left. The reaction mixture was filtered, evaporated to an oil in vacuo, taken up in ether, washed with dilute HCl, dried ($Na_2SO_4$), and evaporated to an oil which was Kugelrohr distilled (130° C., 0.5 mm) to yield 1.42 g (70% yield) clear, colorless oil.

NMR ($CDCl_3$, TMS) δ 3.32 (S, 1H, exchangeable with $D_2O$ wash), 2.72 (S,2H), 1.9–1.1 (b,10H) MS: m/e 139, 79, 40.

EXPERIMENTAL EXAMPLE 3

Demonstrating the Preparation of
1-(2-Aminoethyl)cyclohexanol (III)

A 500 ml Parr pressure vessel was charged with 200 ml acetic acid, 3 g. 5% Rh/C (Engelhardt) 1.5 weight % metal, and shaken under $H_2$ (50 psi) for 10 minutes. To this reaction mixture was added, in seven portions at 30–60 minute intervals, a solution of 10 g. (0.072 mol) 13 in 50 ml acetic acid. When $H_2$ uptake ceased ($\sim 2$ hours after last addition), the reaction mixture was filtered, concentrated in vacuo, dissolved in water, washed once with ether, basified with 50% NaOH, and extracted (5X 30 ml) with $CH_2Cl_2$. The combined organic fractions were dried ($Na_2SO_4$) and evaporated to yield a yellow oil. Kugelrohr distillation (130° C., 0.5 mm) afforded 8.64 g. (0.06 mol, 84% yield).

NMR ($CDCl_3$, TMS) δ 3.01 (t,J=6 Hz, 2H), 2.70 (S,3H, exchangeable with $D_2O$ wash) 2.0–1.0 (b,12H). MS (E30013BE) m/e 143, 125, 82.

EXPERIMENTAL EXAMPLE 4

Demonstrating the Preparation of
N-[2-(1-Hydroxy-1-cyclohexyl)ethyl]-4-methoxybenzeneacetamide (IV) and
N-[2-(cyclohexen-1-yl)ethyl]4-methoxybenzeneacetamide (V)

To 20 ml hot xylene (under an $N_2$ blanket) was added 1 gm (0.007 mol) hydroxyamine (III), and the solution was azeotroped dry by distilling out about 3–5 ml xylene. The reaction mixture was then cooled to 40° C. and 1.27 gm (0.0077 mol, 110 mol %) 4-methoxyphenylacetic acid was added. The reaction mixture was then heated to reflux, azeotroping out water, under $N_2$. After 16 hours, TLC (silica gel, eluted with 3% ethanol in chloroform) showed the starting materials to have been consumed, and the products IV and V to have been generated. The reaction mixture was cooled, washed with saturated $Na_2CO_3$ solution, then with dilute (3%) HCl. Ethyl acetate was added to the organic phase to prevent an oil from separating out of solution. The organic phase was then washed with brine, dried over $Na_2SO_4$, and evaporated to yield 2.06 g. (100% yield) yellow oil. After standing overnight, the oil solidified. HPLC analysis showed the mixture to contain 19:81 ratio of V to IV. (Ultrasphere-octyl reverse phase column, eluted with 60% methanol, 40% water, UV detector set at 270 nm.)

A sample of IV was isolated by preparative TLC (silica gel, eluted with 3% ethanol in chloroform).

Anal. Calcd. for $C_{17}H_{25}NO_3$: C, 70.07; H, 8.64; N, 4.80. Found: C, 70.07; H, 8.60; N, 4.97 (A.S. No. 81-7222).

Mass spectrum, m/e 291, 273 (−$H_2O$), 166, 152, 121, 109 (A.S. No. F81286). NMR ($CDCl_3$) δ 1–2 (b, 12H), 3.14 (S,2H, Ar—$CH_2$), 3.27 (S,1H,OH), 3.40 (m,2H,$CH_2$—N), 3.76 (S,3H,$OCH_3$), 6.7 (bm,1H,NH), 6.94 (dd,4H,J=12 Hz, 8 Hz).

EXPERIMENTAL EXAMPLE 5

Demonstrating the Dehydration of the Mixture of IV and V to Obtain Predominantly V To 25 ml dimethylsulfoxide, under an $N_2$ blanket, was added 1 g. of a mixture of IV and V. The reaction mixture was then heated between 100° and 110° C. for three hours. The reaction was then added to 50 ml $H_2O$ and extracted 3X 25 ml ether. The combined ether layers were then washed (2X 20 ml brine), dried ($Na_2SO_4$), and evaporated to yield 0.91 g. crystalline solid. Recrystallization from ethyl acetate-heptane afforded 0.88 g of V. This compound was identical (IR, NMR, MS, mixed melting point, GC retention time) to the known material produced by literature methods.

The invention has been described in detail with particular reference to preferred embodiments thereof, but it will be understood that variations and modifications can be effected within the spirit and scope of the invention.

I claim:

1. Process for the preparation of a compound having the formula

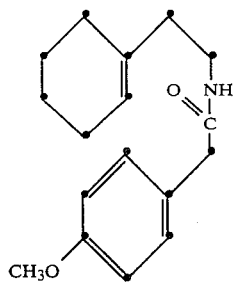

which comprises the steps of
(A) hydrogenating 2-cyano-1-oxaspiro[2]nonane in the presence of a hydrogenation catalyst to obtain 1-cyanomethylcyclohexanol, wherein the hydrogenation is discontinued after the uptake of about one mole equivalent of hydrogen;
(B) hydrogenating the product of Step (A) in the presence of a hydrogen treated rhodium catalyst suspended in an acidic solvent to obtain 1-(2-aminoethyl)cyclohexanol;
(C) reacting the product of Step (B) with 4-methoxyphenylacetic acid to obtain a mixture of compounds comprising N-[2-(1-hydroxy-1-cyclo-hexyl)ethyl]-4-methoxybenzeneacetamide and N-[2-(cyclohexen-1-yl)ethyl]-4-methoxybenzene acetamide;
(D) dehydrating the product mixture of Step (C).

2. Process according to claim 1 wherein the hydrogenation catalyst in Step (A) is platinum, palladium or Raney nickel.

3. Process according to claim 1 wherein the catalyst in Step (A) is supported on silica, alumina, carbon, calcium sulfate or barium sulfate and the catalyst in Step (B) is supported on silica, alumina or carbon.

4. Process according to claim 1 wherein the catalyst in Step (A) is present in amount of from about 1 to 2.0 weight percent and the catalyst in Step (B) is present in an amount of from about 0.1 to 2.5 weight percent, the weight of both catalysts being based on the amount of the material being hydrogenated.

5. Process according to claim 1 wherein the product of Step (A) is added to the solvent-catalyst mixture after contacting the catalyst with hydrogen, the rate of addition of said product of Step (A) being controlled to achieve maximum formation of hydroxyamine.

6. Process according to claim 1 wherein Step (A) is conducted in the presence of a $C_1$–$C_4$ alkanol solvent or a $C_1$–$C_4$ aliphatic carboxylic acid solvent and the solvent in Step (B) is a $C_1$–$C_4$ aliphatic carboxylic acid or a combination of a $C_1$–$C_4$ alkanol and an inorganic acid.

7. Process according to claim 1 wherein Step (C) is conducted under an inert atmosphere in an inert solvent capable of forming an azeotropic mixture with water.

8. Process according to claim 1 wherein the dehydration of the product mixture of Step (C) is achieved by heating the mixture in the presence of dimethylsulfoxide.

9. Process according to claim 1 wherein the catalyst of Step (A) is present in an amount of about 1.0 weight percent and the catalyst of Step B is present in an amount of about 1.5 weight percent, the weight of both catalysts being based on the weight of the material being hydrogenated.

10. Process for the preparation of a compound having the formula

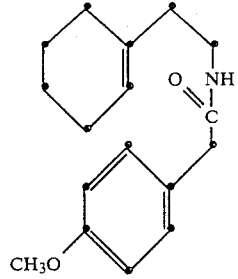

which comprises the steps of
(A) hydrogenating 2-cyano-1-oxaspiro[2]nonane in the presence of a platinum, palladium or Raney nickel catalyst to obtain 1-cyanomethylcyclohexanol, wherein the hydrogenation is discontinued after the uptake of about one mole equivalent of hydrogen;
(B) hydrogenating the product of Step (A) under pressure in the presence of a hydrogen treated rhodium catalyst suspended in an acidic solvent to obtain 1-(2-aminoethyl)-cyclohexanol;
(C) reacting the product of Step (B) with 4-methoxyphenylacetic acid to obtain a mixture of compounds comprising N-[2-(1-hydroxy-1-cyclohexyl)ethyl]-4-methoxybenzenacetamide and N-[2-(cyclohexen-1-yl)ethyl]-4-methoxybenzene acetamide;
(D) dehydrating the product mixture of Step (C).

11. Process according to claim 10 wherein the catalyst in Step (A) is present in an amount of about 0.1 to 2.0 weight percent and the catalyst in Step (B) is present in an amount of from about 0.1 to about 2.5 weight percent, the weight of both catalysts being based on the amount of material being hydrogenated.

12. Process according to claim 10 wherein Step (B) is carried out under a hydrogenation pressure of about 50 to 100 psig.

13. Process according to claim 10 wherein the product of Step (A) is added to the solvent-catalyst mixture after contacting the catalyst with hydrogen.

14. Process according to claim 13 wherein the rate of addition of said product of Step (A) is controlled to achieve maximum formation of hydroxyamine.

15. Process according to claim 9 wherein the solvent in Step (A) is selected from the group consisting of methanol, ethanol, 1-propanol, 2-propanol, n-butanol, iso-butanol and t-butanol and the solvent in Step (B) is acetic acid, propanoic acid, butyric acid or a combination of an alkanol and inorganic acid wherein the alkanol is methanol, ethanol, 1-propanol, 2-propanol, n-butanol, iso-butanol or t-butanol and the inorganic acid is sulfuric acid or hydrochloric acid.

16. Process according to claim 10 wherein dehydration of the product mixture of Step (C) is achieved by heating the mixture in the presence of about 1–10 moles of dimethylsulfoxide per mole of the product mixture of Step (C).

* * * * *